US008820164B2

(12) United States Patent
Voor, Jr.

(10) Patent No.: US 8,820,164 B2
(45) Date of Patent: Sep. 2, 2014

(54) RETROREFLECTOR FOR ULTRASONIC INSPECTION

(75) Inventor: James A. Voor, Jr., Thomaston, CT (US)

(73) Assignee: Sikorsky Aircraft Corporation, Stratford, CT (US)

( * ) Notice: Subject to any disclaimer, the term of this patent is extended or adjusted under 35 U.S.C. 154(b) by 221 days.

(21) Appl. No.: 13/362,840

(22) Filed: Jan. 31, 2012

(65) Prior Publication Data

US 2013/0192374 A1 Aug. 1, 2013

(51) Int. Cl.
*G01B 17/02* (2006.01)
*G01N 9/24* (2006.01)

(52) U.S. Cl.
USPC .............................................. 73/627; 73/614

(58) Field of Classification Search
USPC ............................. 73/627, 787–790
See application file for complete search history.

(56) References Cited

U.S. PATENT DOCUMENTS

| 4,271,706 A * | 6/1981 | Ledley ............................. 73/614 |
| 4,596,006 A | 6/1986 | Eder |
| 4,907,888 A | 3/1990 | Clarke et al. |
| 5,959,774 A | 9/1999 | Benson et al. |
| 6,742,903 B2 | 6/2004 | Canning |
| 6,847,584 B2 | 1/2005 | Deason et al. |
| 7,450,250 B2 | 11/2008 | Venkatesh et al. |
| 2002/0129654 A1* | 9/2002 | Hongerholt ..................... 73/596 |
| 2006/0049721 A1 | 3/2006 | Kuehnicke |
| 2007/0186655 A1* | 8/2007 | Reed et al. ...................... 73/620 |
| 2012/0191377 A1* | 7/2012 | Engl et al. ...................... 702/39 |

FOREIGN PATENT DOCUMENTS

EP WO2011/039339 * 4/2011

* cited by examiner

*Primary Examiner* — Julio J Maldonado
*Assistant Examiner* — Sheikh Maruf
(74) *Attorney, Agent, or Firm* — Cantor Colburn LLP

(57) ABSTRACT

A system for ultrasonic inspection of a structure includes a transducer located at a first surface of the structure to transmit an ultrasonic signal from the transducer through the first surface to a second surface of the structure located substantially opposite the first surface. A plurality of retroreflector elements are located at the second surface to reflect the ultrasonic signal back toward the transducer. A method of ultrasonic inspection of a structure includes transmitting an ultrasonic signal from a transducer located at a first surface of the structure toward a second surface of the structure located substantially opposite the first surface. The ultrasonic signal is reflected back toward the transducer via a plurality of retroreflector elements disposed at the second surface.

20 Claims, 5 Drawing Sheets

RETROREFLECTOR FOR ULTRASONIC INSPECTION

BACKGROUND OF THE INVENTION

The subject matter disclosed herein relates to ultrasonic inspection. More specifically, the subject disclosure relates to ultrasonic inspection of components having complex geometries and/or contours.

Modern aircraft include many components formed from composites constructed via a layup and cure of a plurality of plies to give the components a selected shape and structural strength. Ultrasonic inspection is typically performed on such components to verify structural integrity of the components and to identify any disbonds, delaminations, foreign object inclusions, etc., in the component. Many other engineering materials also require ultrasonic inspection to verify structural integrity and to identify cracks, seams, stringers, shrinkage, bursts, porosity, lack of fusion, non-metallic inclusions etc. In ultrasonic inspection, an ultrasound transducer connected to a diagnostic machine is passed over the component being inspected. The transducer is typically coupled to the component by a thin layer of couplant (such as water or oil). Often, the transducers are coupled to the component through a water bath, as in immersion inspection. There are two methods of receiving the ultrasound waveform, reflection and attenuation. In reflection (or pulse-echo) mode, the transducer, often a hand-held unit or "hand scanner", performs both the sending and the receiving of the pulsed waves as the signal is reflected back to the device. Reflected ultrasound comes from an interface, such as the back wall of the component or from an imperfection within the component. The diagnostic machine displays these results in the form of a signal with an amplitude representing the intensity of the reflection and the distance, representing the arrival time of the reflection. The display may also be in the form of a planar or cross sectional image with colors representing reflectors or degrees of signal attenuation. Complex shapes of the component, such as ply drop offs, contours, and curvature mismatches between a front surface (where the transducer is located) and a back surface of the component, make reflection mode inspection of such components difficult at best, requiring constant manipulation of the transducer position in order to monitor the amplitude of the signal reflected from the back wall. Such manipulation results in a less than reliable inspection of the component, such as false positives, false negatives and mislocation of defects, etc.

The present method for scanning components having complex shapes and lacking parallel front and back wall surfaces is through the use of computerized multi axis ultrasonic scanning machines. Sensor scan paths for a component are programmed into a motion controller. Angles of reflection and refraction of the scanning beam in or through the component must be calculated in order to position the ultrasonic sensors properly. Programming the motion controller to scan a complex shaped part is extremely labor intensive.

An alternative method for inspecting complex components is attenuation (or through-transmission) mode. In attenuation mode, a transmitter sends ultrasound through one surface, and a separate receiver detects the amount that has reached it on another surface after traveling through the medium. Imperfections or other conditions in the space between the transmitter and receiver reduce the amount of sound transmitted, thus revealing their presence. Using the couplant increases the efficiency of the process by reducing the losses in the ultrasonic wave energy due to separation between the surfaces. Inspection via attenuation mode is typically performed with the component submerged in an immersion tank, and motion of the transmitter and receiver is controlled via a scan program to inspect selected portions of, or the entire component. Immersion tank equipment is quite expensive compared to equipment required for reflection mode inspection, and further requires development of complex scanning programs for the transmitter and receiver.

BRIEF DESCRIPTION OF THE INVENTION

According to one aspect of the invention, a system for ultrasonic inspection of a structure includes a transducer located at a first surface of the structure to transmit an ultrasonic signal from the transducer through the first surface to a second surface of the structure located substantially opposite the first surface. A plurality of retroreflector elements are located at the second surface to reflect the ultrasonic signal back toward the transducer.

According to another aspect of the invention, a method of ultrasonic inspection of a structure includes transmitting an ultrasonic signal from a transducer located at a first surface of the structure toward a second surface of the structure located substantially opposite the first surface. The ultrasonic signal is reflected back toward the transducer via a plurality of retroreflector elements disposed at the second surface.

These and other advantages and features will become more apparent from the following description taken in conjunction with the drawings.

BRIEF DESCRIPTION OF THE DRAWINGS

The subject matter, which is regarded as the invention, is particularly pointed out and distinctly claimed in the claims at the conclusion of the specification. The foregoing and other features, and advantages of the invention are apparent from the following detailed description taken in conjunction with the accompanying drawings in which:

The detailed description explains embodiments of the invention, together with advantages and features, by way of example with reference to the drawings.

DETAILED DESCRIPTION OF THE INVENTION

Figure 1:
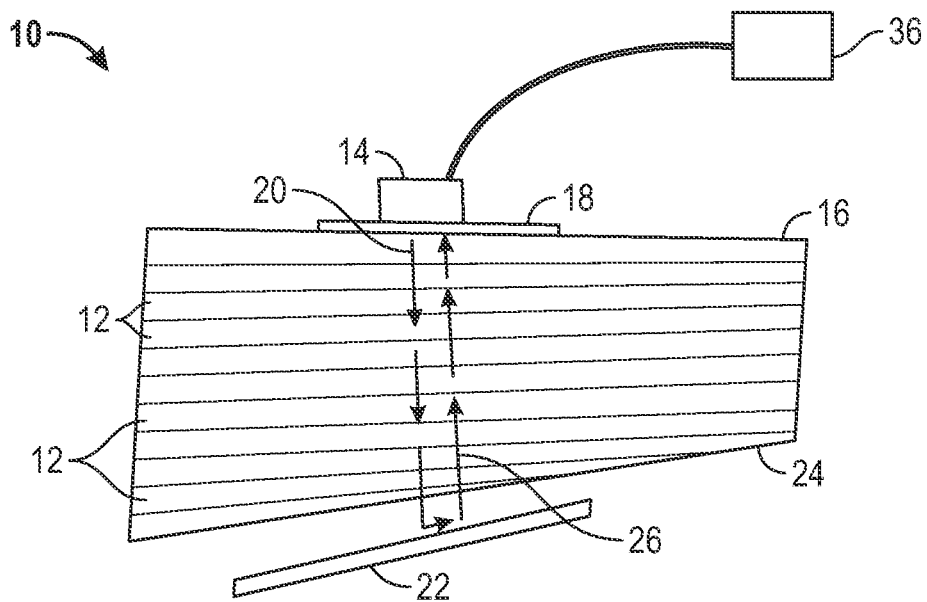
FIG. 1 is a cross-sectional view of an embodiment of a composite structure.

Shown in FIG. 1 is an embodiment of a composite structure 10. The structure 10 includes a plurality of composite plies 12 cured together to form the structure 10. To ultrasonically inspect the composite structure 10, an ultrasonic transducer 14 is positioned at a first surface 16 of the composite structure 10. The transducer 14 is separated from the composite structure 10 by a couplant 18, which may be, for example, an oil or water. In this embodiment, the ultrasonic transducer 14 is configured to transmit an ultrasonic signal 20 into the composite structure 10.

Figure 2:
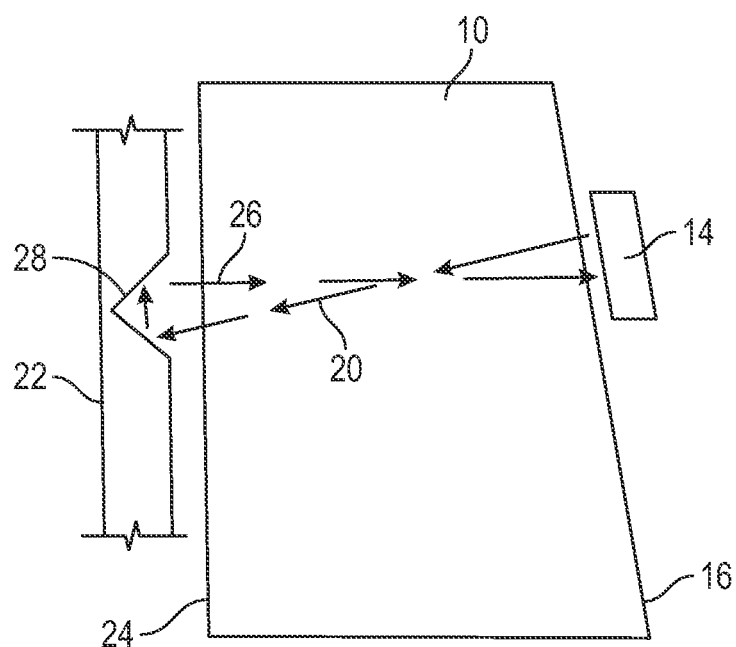
FIG. 2 is an illustration of an embodiment of a retroreflector shape for ultrasonic inspection.
Figure 3:
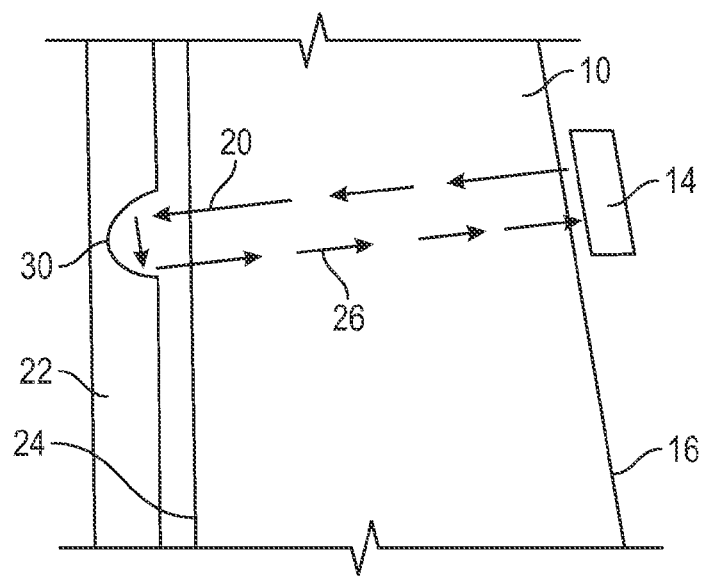
FIG. 3 is an illustration of another embodiment of a retroreflector shape for ultrasonic inspection.
Figure 4:
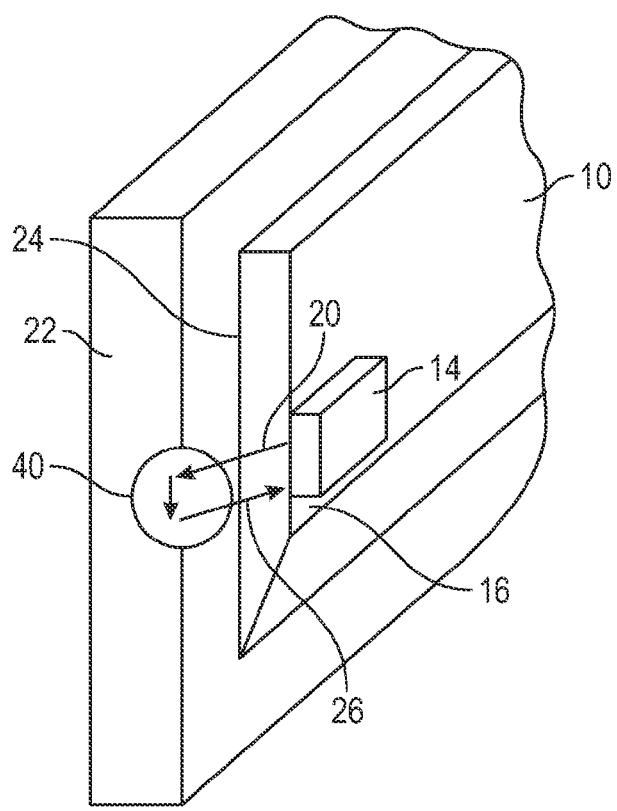
FIG. 4 is an illustration of yet another embodiment of a retroreflector shape for ultrasonic inspection.
Figure 5:
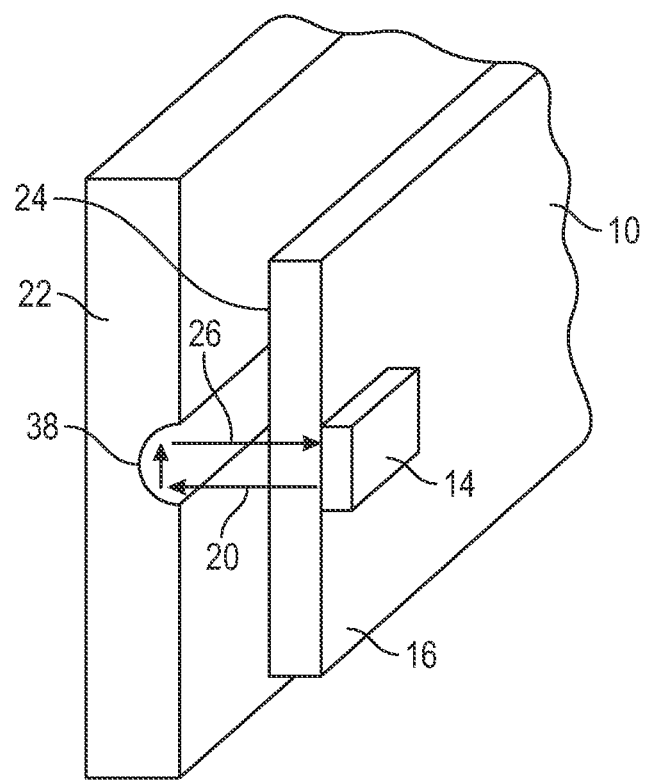
FIG. 5 is an illustration of still another embodiment of a retroreflector shape for ultrasonic inspection.

A retroreflector panel 22 is disposed at a second surface 24 of the composite structure 10, substantially opposite the first surface 16. As with the first surface 14, a layer couplant 18 may be located between the second surface 24 and the retroreflector panel 22. The retroreflector panel 22 reflects the ultrasonic signal 20 transmitted by the transducer 14 back to the transducer 14 as a reflected signal 26. The reflected signal 26 is received by the transducer 14 and processed by a diagnostic unit 36 to determine the presence of any defects or other anomalies in the structure. The function of the retroreflector panel 22 is independent of the relative orientations of the retroreflector panel 22 and the transducer 14, so that the reflected signal 26 will be directed to the transducer 14 in instances such as when the first surface 16 and the second surface 24 are not parallel, or when the transducer 14 and the retroreflector panel 22 are not located on parallel planes. Referring now to FIG. 2, the retroreflector panel 22 may comprise a plurality of pyramidal shapes 28 arrayed on the retroreflector panel 22, or as shown in FIG. 3, the retroreflector panel 22 may be formed from a plurality of conical shapes 30. Further, as shown in FIGS. 4 and 5, the retroreflector panel 22 may be formed from a plurality of hemispherical shapes 40 or grooves 38. The size and depth of the hemispherical shapes 40, grooves 38, pyramidal shapes 28 or the conical shapes 30 may depend on the frequency of the ultrasonic signal 20.

Figure 6:
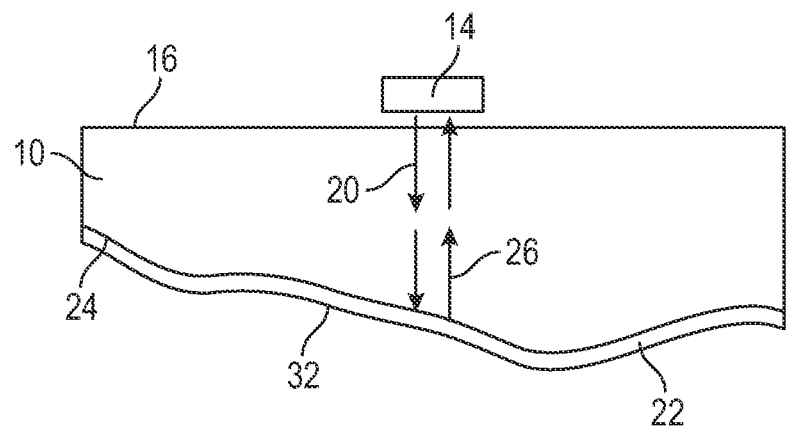
FIG. 6 is an illustration of an embodiment of a retroreflector sheet.

Referring now to FIG. 6, the retroreflector panel 22 may comprise a conformal sheet 32, foil material or a molded plastic sheet, in which the grooves 38, hemispherical shapes 36, pyramidal shapes 28 or conical shapes 30 are embedded. The conformal sheet 32 is applied to and secured to the second surface 24.

Although the embodiments described herein are related to the ultrasonic inspection of a composite structure 10, it is to be appreciated that the retroreflector panel 22 may be utilized in the ultrasonic inspection of structures formed form other materials, such as a metallic structure. Further, the retroreflector panel 22 may be utilized in reflector mode ultrasonic inspection via a hand scanner, or via an immersion tank (not shown).

Figure 7:
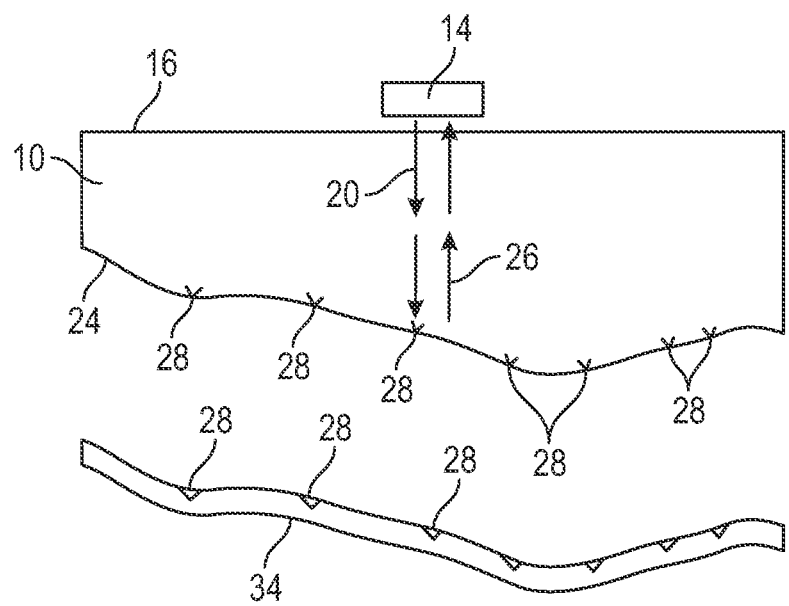
FIG. 7 is an illustration of an embodiment of a retroreflector peel ply for ultrasonic inspection.

In another embodiment, as shown in FIG. 7, the composite structure 10 is formed with a peel ply 34. The peel ply 34 is applied at the second surface 24, and includes retroreflector elements, for example, pyramidal shapes 28 or conical shapes 30 or hemispherical shapes 40 or grooves 38, in relief. The peel ply 34 is applied before cure of the composite structure 10, such that the retroreflector element shapes are cured into the second surface 24. After cure of the composite structure 10, the peel ply 34 is removed and the retroreflector elements are then utilized during ultrasonic inspection to reflect the ultrasonic signal 20 toward the transducer 14 thus improving accuracy of the ultrasonic inspection.

In another embodiment, the cured composite structure 10 has a temporary retroreflective panel 22 of pyramidal shapes 28, conical shapes 30, grooves 38, or hemispherical shapes 40 acoustically coupled to the second surface 24. This retroreflective panel 22 may be formed from a paste, adhesive, epoxy, latex, putty, wax or any substance that could be wiped, dissolved or scraped etc. away after use.

Figure 8:
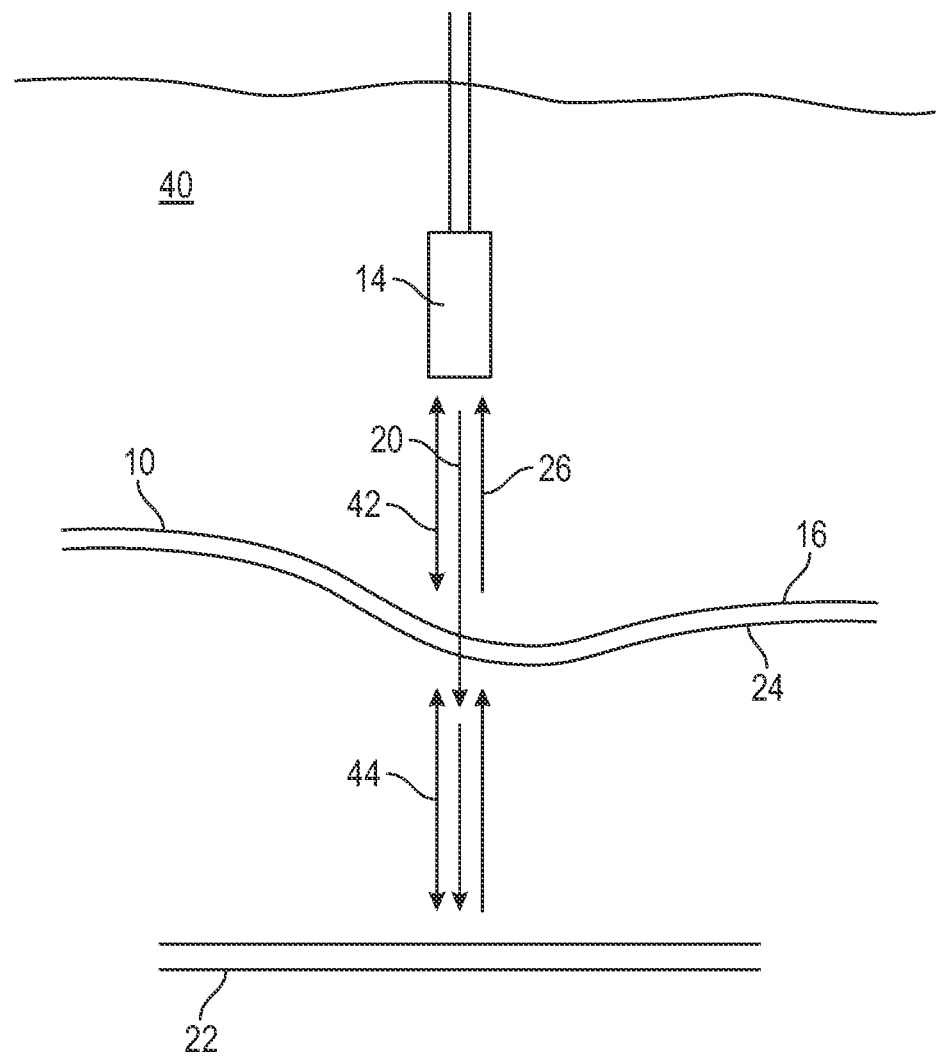
FIG. 8 is an illustration of an embodiment of a retroreflector plate for immersion testing.

Referring now to FIG. 8, the retroreflector panel 22 is a reflector plate utilized in immersion testing of the composite structure 10. In immersion testing, the composite structure 10 and the transducer 14 are immersed in a water bath 40. The transducer 14 is positioned at a transmission distance 42 from the first surface 16, and the retroreflector panel 22 is positioned as a reflector plate at a reflector distance 44 from the second surface 24. The retroreflector panel 22 includes the grooves 38, hemispherical shapes 36, pyramidal shapes 28 or conical shapes 30. Utilization of the retroreflector panel 22 in place of a typical reflector plate, especially in inspection of composite structures 10 having complex geometries greatly increases the accuracy of the ultrasonic inspection. Further, while a substantially planar retroreflector panel 22 is shown, it is to be appreciated that the retroreflector panel 22 may be shaped or contoured to improve the reflected signal 26.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

The invention claimed is:

1. A system for ultrasonic inspection of a structure comprising:
   a transducer disposed at a first surface of the structure to transmit an ultrasonic signal from the transducer through the first surface to a second surface of the structure located substantially opposite the first surface, the first surface disposed between the transducer and the second surface; and
   a plurality of retroreflector elements disposed at the second surface to reflect the ultrasonic signal toward the transducer.

2. The system of claim 1, wherein the plurality of retroreflector elements are disposed at a retroreflector panel located at the second surface.

3. The system of claim 1, wherein the plurality of retroreflector elements are disposed at a conformal retroreflector sheet located at the second surface.

4. The system of claim 3, wherein the retroreflector sheet substantially conforms to a contour of the second surface.

5. The system of claim 1, wherein the plurality of retroreflector elements are formed integral to the second surface.

6. The system of claim 5, wherein the structure is a composite structure.

7. The system of claim 6, wherein the plurality of retroreflector elements are formed during cure of the composite structure.

8. A system for ultrasonic inspection of a structure comprising:
   a transducer disposed at a first surface of the structure to transmit an ultrasonic signal from the transducer through the first surface to a second surface of the structure located substantially opposite the first surface, the first surface disposed between the transducer and the second surface; and
   a plurality of retroreflector elements disposed at the second surface to reflect the ultrasonic signal toward the transducer;
   wherein the plurality of retroreflector elements are formed integral to the second surface, the structure is a composite structure, the plurality of retroreflector elements are formed during cure of the composite structure, via application of a removable peel ply to the composite structure.

9. The system of claim 1, wherein the plurality of retroreflector elements comprise a plurality of pyramidal elements.

10. The system of claim 1, wherein the plurality of retroreflector elements comprise a plurality of conical, hemispherical or groove elements.

11. A method of ultrasonic inspection of a structure comprising:

transmitting an ultrasonic signal from a transducer located at a first surface of the structure toward a second surface of the structure located substantially opposite the first surface, the first surface disposed between the transducer and the second surface; and reflecting the ultrasonic signal toward the transducer via a plurality of retroreflector elements disposed at the second surface.

12. The method of claim 11, further comprising receiving the ultrasonic signal at the transducer.

13. The method of claim 12, further comprising processing the signal at a diagnostic unit.

14. The method of claim 11, wherein the plurality of retroreflector elements are disposed at a retroreflector panel located at the second surface.

15. The method of claim 11, wherein the plurality of retroreflector elements are disposed at a conformal retroreflector sheet located at the second surface and substantially conforming thereto.

16. The method of claim 11, wherein the plurality of retroreflector elements are formed integral to the second surface.

17. The method of claim 16, wherein the plurality of retroreflector elements are formed via application of a removable peel ply to the second surface.

18. The method of claim 11, wherein the plurality of retroreflector elements comprise a plurality of pyramidal elements.

19. The method of claim 11, wherein the plurality of retroreflector elements comprise a plurality of conical elements.

20. The method of claim 11, wherein the plurality of retroreflector elements comprise a plurality of hemispherical elements.

\* \* \* \* \*